United States Patent [19]

Holmwood et al.

[11] Patent Number: 4,548,945

[45] Date of Patent: Oct. 22, 1985

[54] FUNGICIDALLY ACTIVE SUBSTITUTED 1-HYDROXYETHYL-TRIAZOLYL DERIVATIVES

[75] Inventors: Graham Holmwood; Jörg Stetter, both of Wuppertal; Karl H. Büchel, Burscheid; Paul Reinecke, Leverkusen; Wilhelm Brandes, Leichlingen; Hans Scheinpflug, Leverkusen, all of Fed. Rep. of Germany

[73] Assignee: Bayer Aktiengesellschaft, Leverkusen, Fed. Rep. of Germany

[21] Appl. No.: 534,233

[22] Filed: Sep. 21, 1983

[30] Foreign Application Priority Data

Oct. 8, 1982 [DE] Fed. Rep. of Germany ....... 3237400

[51] Int. Cl.[4] ............... A01N 43/64; A01N 59/16; C07D 249/08; C07F 3/00
[52] U.S. Cl. .................... 514/383; 514/184; 514/189; 548/101; 548/262; 549/370; 549/444; 549/555; 549/559
[58] Field of Search ................ 548/101, 262; 424/245, 424/269

[56] References Cited

U.S. PATENT DOCUMENTS 4,472,416 9/1984 Stetter et al. ............ 548/262

FOREIGN PATENT DOCUMENTS 0040345 11/1981 European Pat. Off. ........... 548/262

Primary Examiner—Alton D. Rollins
Attorney, Agent, or Firm—Sprung Horn Kramer & Woods

[57] ABSTRACT

Substituted 1-hydroxyethyl-triazole derivatives of the formula

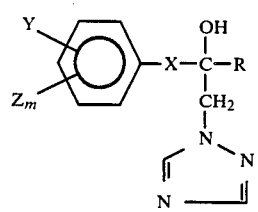

in which
R represents optionally substituted alkyl, optionally substituted cycloalkyl or optionally substituted phenyl,
X represents the grouping —$OCH_2$—, —$SCH_2$—, —$(CH_2)_p$— or —CH=CH—,
Y represents the grouping —CO—$Y^1$ or an acetal or ketal derivative thereof, or the grouping —C($Y^1$)-=N—$OY^2$,
$Y^1$ represents hydrogen, alkyl, alkenyl, alkinyl, optionally substituted cycloalkyl, optionally substituted phenyl or optionally substituted benzyl,
$Y^2$ represents hydrogen, alkyl, alkenyl, alkinyl, optionally substituted cycloalkyl or optionally substituted benzyl,
Z represents halogen, alkyl, alkoxy, alkylthio, halogenoalkyl, halogenoalkoxy or halogenoalkylthio and
the indices m and p represent 0, 1 or 2, or addition products thereof with acids or metal salts which possess fungicidal activity.

8 Claims, No Drawings

FUNGICIDALLY ACTIVE SUBSTITUTED 1-HYDROXYETHYL-TRIAZOLYL DERIVATIVES

The present invention relates to new substituted 1-hydroxyethyl-triazolyl derivatives, several processes for their preparation and their use as fungicides.

It has already been disclosed that 3,3-dimethyl-1-phenoxy-2-(1,2,4-triazol-1-yl-methyl)-2-butanols have good fungicidal properties (compare U.S. application Ser. No. 260,479, filed May 4, 1981, abandoned. However, the action of these compounds is not always completely satisfactory, especially when low amounts and concentrations are applied.

New substituted-1-hydroxyethyl-triazolyl derivatives of the general formula

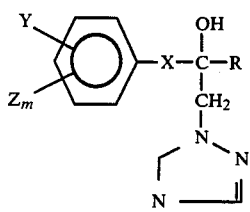

in which
  R represents optionally substituted alkyl, optionally substituted cycloalkyl or optionally substituted phenyl,
  X represents the grouping —OCH$_2$—, —SCH$_2$—, —(CH$_2$)p— or —CH=CH—,
  Y represents the grouping —CO—Y$^1$ or an acetal or ketal derivative thereof, or the grouping —C(Y$^1$)=N—OY$^2$,
  Y$^1$ represents hydrogen, alkyl, alkenyl, alkinyl, optionally substituted cycloalkyl, optionally substituted phenyl or optionally substituted benzyl, Y$^2$ represents hydrogen, alkyl, alkenyl, alkinyl, optionally substituted cycloalkyl or optionally substituted benzyl,
  Z represents halogen, alkyl, alkoxy, alkylthio, halogenoalkyl, halogenoalkoxy or halogenoalkylthio and
  the indices m and p represent 0, 1 or 2,
and acid addition salts and metal salt complexes thereof have been found.

The compounds of the formula (I) possess an asymmetric carbon atom and can therefore be obtained in the two optical isomer forms. The compounds of the formula (I) may also occur in the form of various geometric isomers, depending on the meaning of the substituents X and Y.

It has furthermore been found that the substituted 1-hydroxyethyl-triazolyl derivatives of the formula (I) are obtained by a process in which
(a) oxiranes of the formula

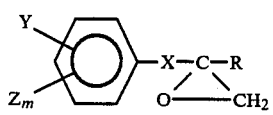

in which
  R, X, Y, Z and m have the abovementioned meaning, are reacted with 1,2,4-triazole of the formula

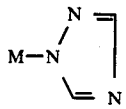

in which
  M represents hydrogen or an alkali metal,
in the presence of a diluent and if appropriate in the presence of a base, or
(b) triazolylmethyl-oxiranes of the formula

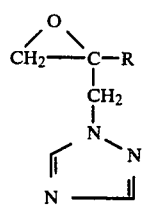

in which
  R has the abovementioned meaning,
are reacted with (thio)phenols of the formula

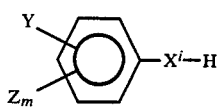

in which
  Y, Z and m have the abovementioned meaning and
  X$^1$ represents oxygen or sulphur,
in the presence of a diluent and if appropriate in the presence of a base, or
(c) the compounds according to the invention which are obtainable by processes (a) and (b) and have the formula

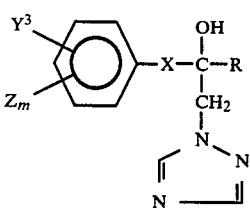

in which
  R, X, Z and m have the abovementioned meaning and
  Y$^3$ represents the grouping —CO—Y$^1$ or an acetal or ketal derivative thereof,
are reacted with hydroxylamine derivatives of the formula

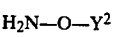

H$_2$N—O—Y$^2$ (VI)

in which
  Y$^2$ has the abovementioned meaning,
in the presence of a diluent, or
(d) the compounds according to the invention which are obtainable by processes (a), (b) and (c) and have the formula

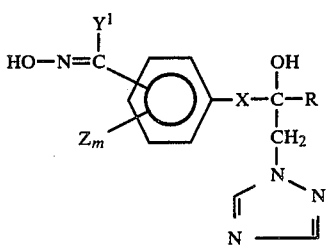

(Ib)

in which

R, X, Y¹, Z and m have the abovementioned meaning, are reacted with halides of the formula $$Y^4-Hal \qquad (VII)$$

in which

Hal represents chlorine, bromine or iodine and
$Y^4$ has the meanings of $Y^2$, with the exception of hydrogen, in the presence of a diluent and if appropriate in the presence of a base.

If desired, an acid or a metal salt can then be added onto the compounds of the formula (I) thus obtained.

It has also been found that the new substituted 1-hydroxyethyl-triazolyl derivatives of the formula (I) have powerful fungicidal properties.

Surprisingly, the substituted 1-hydroxyethyl-triazolyl derivatives of the formula (I) according to the invention display better fungicidal actions than the abovementioned 3,3-dimethyl-1-phenoxy-2-(1,2,4-triazol-1-yl-methyl)-2-butanols which are known from the prior art and are closely related compounds structurally and from the point of view of their action. The active compounds according to the invention thus represent an enrichment of the art.

Formula (I) provides a general definition of the substituted 1-hydroxyethyl-triazolyl derivatives according to the invention. Preferably, in this formula, R represents straight-chain or branched alkyl with 1 to 4 carbon atoms, or represents cycloalkyl which has 3 to 7 carbon atoms and is optionally mono- or poly-substituted by identical or different substituents, substituents which may be mentioned being: halogen, alkyl with 1 to 4 carbon atoms and alkoxy with 1 or 2 carbon atoms, or represents phenyl which is optionally mono- or poly-substituted by identical or different substituents, possible substituents being the substituents on phenyl mentioned for $R^3$, or represents the grouping

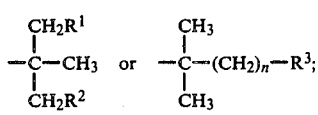

$R^1$ represents hydrogen or halogen,
$R^2$ represents halogen;
$R^3$ represents alkyl, alkoxy or alkylthio with in each case 1 to 4 carbon atoms, or represents halogenoalkoxy or halogenoalkylthio with in each case 1 or 2 carbon atoms and 1 to 5 identical or different halogen atoms, such as fluorine and chlorine atoms, or represents alkenyl with 2 to 6 carbon atoms, or represents alkoxycarbonyl with 1 to 4 carbon atoms in the alkyl part, or represents cyano or in each case optionally mono- or poly-substituted phenyl, phenoxy, phenylthio, phenylalkoxy with 1 to 4 carbon atoms in the alkyl part or phenylalkylthio with 1 to 4 carbon atoms in the alkyl part, preferred substituents on the phenyl which may be mentioned in each case being: halogen, alkyl with 1 to 4 carbon atoms; alkoxy and alkylthio with in each case 1 or 2 carbon atoms; halogenoalkyl, halogenoalkoxy and halogenoalkylthio with in each case 1 or 2 carbon atoms and 1 to 5 identical or different halogen atoms, such as, in particular, fluorine and chlorine atoms, cyclohexyl, dialkylamino with 1 to 4 carbon atoms in each alkyl part, nitro, cyano, alkoxycarbonyl with 1 to 4 carbon atoms in the alkyl part and optionally halogen-substituted phenyl, n represents the number 0, 1 or 2;
X represents the grouping —OCH₂—, —SCH₂—, —(CH₂)$_p$— or —CH=CH—;
Y represents the grouping —CO—Y¹, —C(OR⁴)₂—Y¹ or

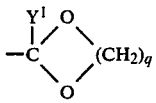

or the grouping —C(Y¹)=N—OY²;

Y¹ represents hydrogen, or represents alkyl with 1 to 4 carbon atoms, or represents alkenyl or alkinyl with in each case 2 to 4 carbon atoms, or represents cycloalkyl which has 3 to 7 carbon atoms and is optionally mono- or poly-substituted by identical or different substituents, substituents which may be mentioned being: halogen, alkyl with 1 to 4 carbon atoms and alkoxy with 1 or 2 carbon atoms, or represents phenyl or benzyl, each of which is optionally mono- or poly-substituted by identical or different substituents, possible substituents being the substituents on phenyl mentioned for $R^3$;

Y² represents hydrogen, or represents straight-chain or branched alkyl with 1 to 4 carbon atoms, or represents alkenyl or alkinyl with in each case 2 to 6 carbon atoms, or represents cycloalkyl which has 3 to 7 carbon atoms and is optionally mono- or poly-substituted by identical or different substituents, substituents which may be mentioned being: halogen, alkyl with 1 to 4 carbon atoms and alkoxy with 1 or 2 carbon atoms, or represents benzyl, which is optionally mono- or poly-substituted by identical or different substituents, possible substituents being the substituents on phenyl mentioned for $R^3$;

$R^4$ represents alkyl with 1 to 4 carbon atoms;
q represents the number 2 or 3;
Z represents halogen, or represents alkyl, alkoxy or alkylthio with in each case 1 to 4 carbon atoms, or represents halogenoalkyl, halogenoalkoxy or halogenoalkylthio with in each case 1 or 2 carbon atoms and 1 to 5 identical or different halogen atoms;
m represents the number 0, 1 or 2, and
p represents the number 0, 1 or 2.

Particularly preferred compounds of the formula (I) are those in which

R represents tert.-butyl or isopropyl, or represents cyclopropyl, cyclopentyl or cyclohexyl, each of which is optionally mono-, di- or tri-substituted by identical or different substituents, substituents which may be mentioned being: methyl, ethyl, isopropyl, methoxy and ethoxy, or represents phenyl which is optionally mono-, di- or tri-substitued by identical or different substituents, substituents which may be mentioned being: fluorine, chlorine, methyl, trifluoromethyl, phenyl and chlorophenyl, or represents the grouping

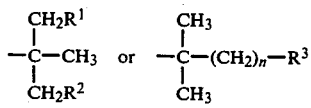

wherein
$R^1$ represents hydrogen, fluorine or chlorine;
$R^2$ represents fluorine or chlorine;
$R^3$ represents methyl, ethyl, propyl, methoxy, ethoxy, methylthio, ethylthio, trifluoromethoxy, trifluoromethylthio, vinyl, methoxycarbonyl, ethoxycarbonyl or cyano, or represents phenyl, phenoxy, phenylthio, phenylmethoxy or phenylmethylthio, each of which is optionally mono- or di-substituted by identical or different substituents, substituents on the phenyl which may be mentioned in each case being: fluorine, chlorine, methyl, ethyl, methoxy, methylthio, trifluoromethyl, trifluoromethoxy, trifluoromethylthio, dimethylamino, methoxycarbonyl and ethoxycarbonyl; and
n represents the number 0, 1 or 2;
X represents the grouping —OCH$_2$—, —SCH$_2$—, —(CH$_2$)$_p$ or —C=CH—;
Y represents the grouping —CO—Y$^1$, —C(OR$^4$)$_2$—Y$^1$ or

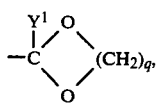

or the grouping —C(Y$^1$)=N—OY$^2$;
wherein
Y$^1$ represents hydrogen, methyl, ethyl or isopropyl, or represents phenyl, which is optionally mono- or di-substituted by identical or different substituents from the group comprising fluorine, chlorine, methyl and trifluoromethyl;
Y$^2$ represents hydrogen, methyl, ethyl, n-propyl, n-butyl, allyl or propargyl, or represents benzyl which is optionally mono- or di-substituted by identical or different substituents from the group comprising fluorine, chlorine, methyl, trifluoromethyl and trifluoromethoxy;
R$^4$ represents methyl, ethyl or propyl; and
q represents the number 2 or 3;
Z represents fluorine, chlorine, bromine, methyl, methoxy, methylthio, trifluoromethyl, trifluoromethoxy or trifluoromethylthio,
m represents the number 0, 1 or 2; and
p represents the number 0, 1 or 2.

Preferred compounds according to the invention also include addition products of acids and those substituted 1-hydroxyethyl-triazolyl derivatives of the formula (I) in which the substituents R, X, Y and Z$_m$ have the meanings which have already been given as preferred for these substituents.

Preferred acids which can be added on include hydrogen halide acids, such as, for example, hydrochloric acid and hydrobromic acid, especially hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and sulphonic acids, such as, for example, p-toluene-sulphonic acid and 1,5-naphthalenedisulphonic acid.

Other preferred compounds according to the invention include addition products of salts of metals of main groups II to IV and of sub-groups I and II and IV to VIII and those substituted 1-hydroxyethyl-triazolyl derivatives of the formula (I) in which the substituents X, Y and Z$_m$ have the meanings which have already been mentioned as preferred for these substituents.

Salts of copper, zinc, manganese, magnesium, tin, iron and nickel are particularly preferred here. Possible anions of these salts are those which are derived from acids which lead to physiologically acceptable addition products. In this connection, particularly preferred acids of this type are the hydrogen halide acids, such as, for example, hydrochloric acid and hydrobromic acid, and furthermore phosphoric acid, nitric acid and sulphuric acid.

If, for example, 2-{2-[4-(1,3-dioxolan-2-yl)-phenyl]-ethenyl}-2-tert.-butyl-oxirane and sodium 1,2,4-triazole are used as starting substances, the course of process (a) according to the invention can be represented by the following equation:

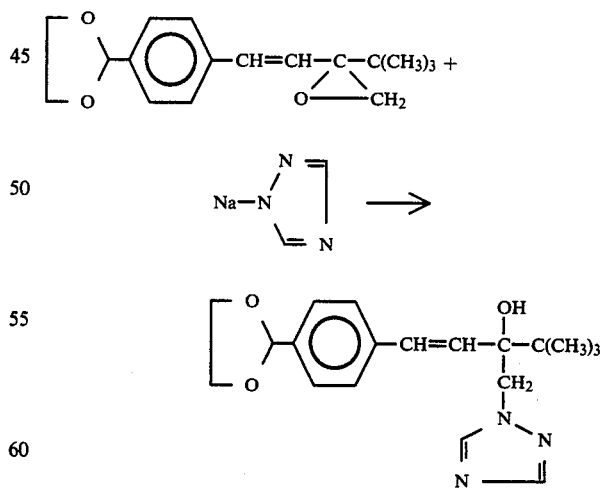

If, for example, 2-tert.-butyl-2-(1,2,4-triazol-1-yl-methyl)-oxirane and p-hydroxyacetophenone are used as starting substances, the course of process (b) according to the invention can be represented by the following equation:

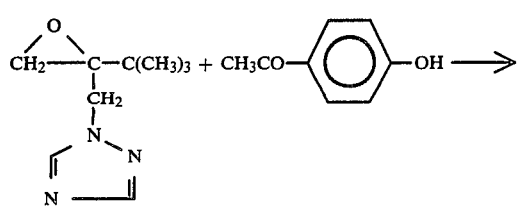

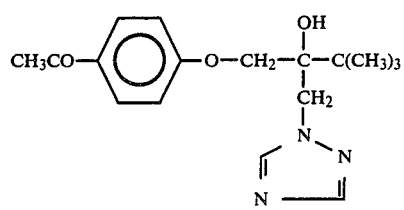

If, for example, 2-(4-acetophenoxymethyl)-3,3-dimethyl-1-(1,2,4-triazol-1-yl)-2-butanol and hydroxylamine hydrochloride are used as starting substances, the course of process (c) according to the invention can be represented by the following equation:

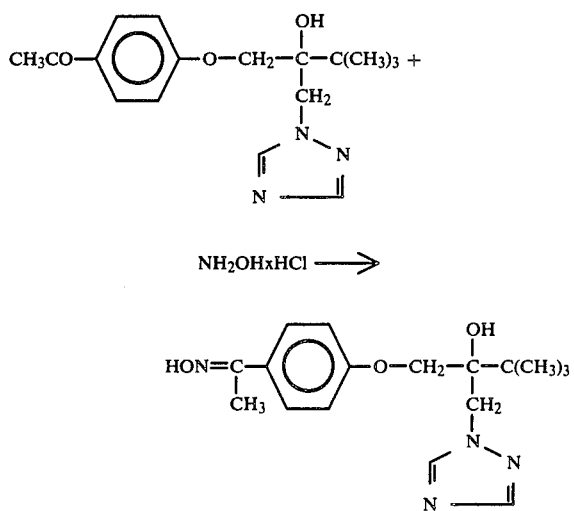

If, for example, 3,3-dimethyl-1-[4-(1-hydroximinoethyl)-phenoxy]-1-(1,2,4-triazol-1-yl)-2-butanol and 2,4-dichlorobenzyl chloride are used as starting substances, the course of process (d) according to the invention can be represented by the following equation:

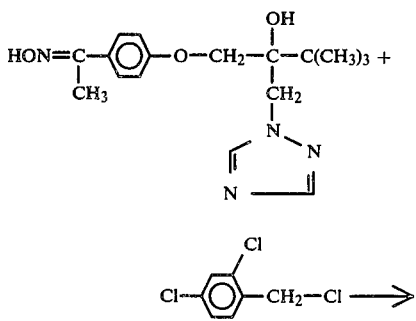

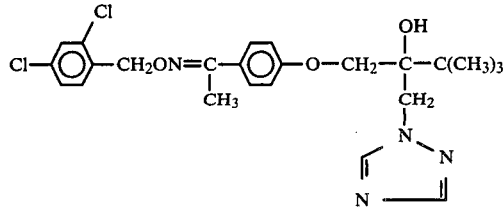

Formula (II) provides a general definition of the oxiranes to be used as starting substances in carrying out process (a) according to the invention. In this formula, R, X, Y and Z and the index m preferably have the meanings which have already been mentioned as preferred for these substituents and for the index m in connection with the description of the substances of the formula (I) according to the invention.

The oxiranes of the formula (II) are not yet known. They are interesting intermediates, and can be obtained in a generally known manner, by a process in which ketones of the formula

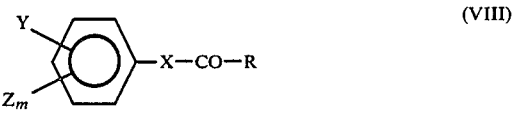 (VIII)

in which

R, X, Y, Z and m have the abovementioned meaning, either (α) are reacted with trimethyloxosulphonium methylide of the formula

 (IX)

in the presence of a diluent, or (β) are reacted with trimethylsulphonium methyl-sulphate of the formula

 (X)

in the presence of an inert organic solvent and in the presence of a base.

The ketones of the formula (VIII) required as starting substances in the preparation of the oxiranes of the formula (II) can be prepared by processes which are known in principle (compare, for example, the preparation examples).

The dimethyloxosulphonium methylide of the formula (VII) required in process variant (α) is known (compare J. Amer. Chem. Soc. 87, 1363–1364 (1965)). In the above reaction, it is processed in the freshly prepared state, by being produced in situ by reaction of trimethyloxosulphonium iodide with sodium hydride, sodium amide or potassium tert.-butylate in the presence of a diluent.

The trimethylsulphonium methylsulphate of the formula (VIII) required in process variant (β) is likewise known (compare Heterocyclus 8, 397 (1977)). In the above reaction, it is likewise employed in the freshly prepared state, by being produced in situ by reaction of dimethylsulphide with dimethylsulphate.

Dimethylsulphoxide is the preferred possible diluent in variant (α) of the process for the preparation of the oxiranes of the formula (II).

The reaction temperatures can be varied within a substantial range in process variant (α) described above. In general, the reaction is carried out at temperatures between 20° C. and 80° C.

The process for the preparation of the oxiranes of the formula (II) by variant (α) and the working up of the reaction mixture obtained in this synthesis are carried out by customary methods (compare J. Amer. Chem. Soc. 87, 1363-1364 (1965)).

Acetonitrile is the preferred possible inert organic solvent in variant (β) for the preparation of the oxiranes of the formula (II).

Strong inorganic or organic bases can be used as the base in process variant (β). Sodium methylate is preferably used.

The reaction temperatures can be varied within a certain range in process variant (β) described above. In general, the reaction is carried out at temperatures between 0° C. and 60° C., preferably at room temperature.

The process for the preparation of the oxiranes of the formula (II) by variant (β) and the working up of the reaction product obtained in this synthesis are carried out by customary methods (compare Heterocycles 8, 397, (1977)).

If appropriate, the oxiranes of the formula (II) can be further reacted directly in the process according to the invention, without being isolated.

Formula (III) provides a general definition of the 1,2,4-triazoles also to be used as starting substances for process (a) according to the invention. In this formula, M preferably represents hydrogen, sodium or potassium.

The 1,2,4-triazoles of the formula (III) are generally known compounds of organic chemistry.

Formula (IV) provides a general definition of the triazolylmethyloxiranes to be used as starting substances in carrying out process (b) according to the invention. In this formula, R preferably has the meanings which have already been mentioned as preferred for this substituent in connection with the description of the substances of the formula (I) according to the invention.

The triazolylmethyloxiranes of the formula (IV) are known (compare U.S. application Ser. No. 352,689, filed Feb. 26, 1982, now U.S. Pat. No. 4,499,281, or they are the subject of U.S. application Ser. No. 458,086, filed Jan. 14, 1983, now abandoned, or they can be obtained in a generally known manner, by a process in which triazolyl-ketones of the formula

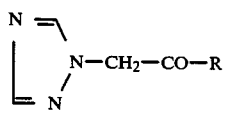

(XI)

in which

R has the abovementioned meaning, are epoxidized in accordance with process variants (α) and (β) described above.

The triazolyl-ketones of the formula (XI) are known (compare DE-OS (German Published Specification) No. 2,431,407, DE-OS (German Published Specification) No. 2,638,470, U.S. Pat. No. 4,344,953, and U.S. patent application Ser. No. 328,871, filed Dec. 8, 1981, now abandoned, or they can be prepared by processes which are known in principle.

Formula (V) provides a general definition of the (thio)phenols also to be used as starting substances for process (b) according to the invention. In this formula, Y, Z and the index m preferably have the meanings which have already been mentioned as preferred for these substituents and for the index m in connection with the description of the substances of the formula (I) according to the invention. $X^1$ preferably represents oxygen or sulphur.

The (thio)phenols of the formula (V) are known, or they are the subject of U.S. application Ser. No. 403,988, filed Aug. 2, 1982, now U.S. Pat. No. 4,472,416, or they can be obtained in a generally customary manner.

The compounds of the formula (Ia) to be used as starting substances in carrying out process (c) according to the invention are substances according to the invention.

Formula (VI) provides a general definition of the hydroxylamine derivatives also to be used as starting substances for process (c) according to the invention. In this formula, $Y^2$ preferably has the meanings which have already been mentioned as preferred for this substituent in connection with the description of the substances of the formula (I) according to the invention.

The hydroxylamines of the formula (VI) are generally known compounds of organic chemistry.

The compounds of the formula (Ib) to be used as starting substances in carrying out process (d) according to the invention are substances according to the invention.

Formula (VII) provides a general definition of the halides also to be used as starting substances for process (d) according to the invention. In this formula, $Y^4$ preferably has the meanings which have already been mentioned as preferred for $Y^2$ in connection with the description of the substances of the formula (I) according to the invention, with the exception of hydrogen.

The halides of the formula (VII) are generally known compounds of organic chemistry.

Possible diluents for processes (a) and (b) according to the invention are organic solvents which are inert under the reaction conditions. These solvents include, preferably, alcohols, such as, for example, ethanol, methoxyethanol or propanol; ketones, such as, for example, 2-butanol; nitriles, such as, for example, acetonitrile; esters, such as, for example, ethyl acetate; ethers, such as, for example, dioxane; aromatic hydrocarbons, such as, for example, benzene and toluene; and amides, such as, for example, dimethylformamide.

Possible bases for the reactions according to the invention are all the inorganic and organic bases which can usually be employed. These include, preferably, alkali metal carbonates, such as, for example, sodium and potassium carbonate; alkali metal hydroxides, such as, for example, sodium hydroxide; alkali metal alcoholates, such as, for example, sodium and potassium methylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out processes (a) and (b) according to the invention. In general, the reactions are carried out at temperatures between 0° and 200° C., preferably between 60° and 150° C.

In carrying out process (a) according to the invention, 1 to 2 mols of azole and, if appropriate, catalytic to 2-molar amounts of base are preferably employed per mol of oxirane of the formula (II); in carrying out process (b) according to the invention, 1 to 2 mols of (thio)-phenol of the formula (V) and, if appropriate, catalytic to 2-molar amounts of base are preferably employed per mol of triazolylmethyl-oxirane of the formula (IV). The end products are in each case isolated in the generally customary manner.

Preferred possible diluents for process (c) according to the invention are alcohols and water, or mixtures of the two.

The reaction temperatures can be varied within a substantial range in process (c). In general, the reaction is carried out between 20° and 120° C., preferably between 50° and 100° C.

In carrying out process (c) according to the invention, 1 to 1.5 mols of hydroxylamine derivative of the formula (VI) are preferably employed per mol of the compound of the formula (Ia). The compounds of the formula (I) are isolated by customary methods.

In a preferred embodiment of process (c), the hydroxylamine derivatives of the formula (VI) are employed in the form of their salts, in particular as hydrochlorides, if appropriate in the presence of an acid-binding agent, such as, for example, sodium acetate (compare also the preparation examples).

Possible diluents for the reaction according to the invention in process (d) are inert organic solvents. These include, preferably, ethers, such as tetrahydrofuran and dioxane; aromatic hydrocarbons, such as toluene and benzene; in individual cases also chlorinated hydrocarbons, such as chloroform, methylene chloride or carbon tetrachloride; and hexamethylphosphoric acid tramide, acid amides, such as dimethylformamide, and sulphoxides, such as dimethylsulphoxide.

If appropriate, the reaction according to the invention in process (d) is carried out in the presence of a strong base. Preferred strong bases include alkali metal amides, hydrides, hydroxides and carbonates, such as, for example, sodium amide, carbonate, hydroxide or hydride and potassium amide, carbonate, hydroxide or hydride, and quaternary ammonium hydroxides and phosphonium hydroxides, such as, for example, tetramethylammonium hydroxide, benzyl-trimethylammonium hydroxide or dibenzyldimethyl-ammonium hydroxide, and tetraphenylphosphonium hydroxide or methyl-triphenyl-phosphonium hydroxide.

The reaction temperatures can be varied within a substantial range in process (d). In general, the reaction is carried out between 20° and 150° C., preferably at room temperature. In individual cases, it is advantageous to carry out the reaction at the boiling point of the solvent, for example, between 60° and 100° C.

In carrying out process (d) according to the invention, 1 to 3 mols of halide of the formula (VII) are preferably employed per mol of the compounds of the formula (Ib). To isolate the end products, the reaction mixture is freed from the solvent, and water and an organic solvent are added to the residue. The organic phase is separated off, and worked up and purified in the customary manner.

In a preferred embodiment of process (d), the reaction according to the invention is carried out in a two-phase system, such as, for example, aqueous sodium hydroxide or potassium hydroxide solution/toluene or methylene chloride, with addition of 0.01–1 mol of a phase transfer catalyst, such as, for example, ammonium or phosphonium compounds, the alcoholates being formed in the organic phase or at the phase boundary and reacting with the halides in the organic phase.

The compounds of the formula (I) obtainable by the process according to the invention can be converted into acid addition salts or metal salt complexes.

The following acids can preferably be used for the preparation of physiologically acceptable acid addition salts of the compounds of the formula (I): the hydrogen halide acids, such as, for example, hydrochloric acid and hydrobromic acid, in particular hydrochloric acid, and furthermore phosphoric acid, nitric acid, sulphuric acid, monofunctional ard bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluene sulphonic acid and 1,5-naphthalenedisulphonic acid.

The acid addition salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are preferably those which are derived from the following acids: hydrogen halide acids, such as, for example, hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as against powdery mildew of barley (*Erysiphe graminis*) and stripe disease of barley (*Drechslera graminea*), and against *Cochliobolus sativus*, and furthermore for combating species of Podosphaera, such as, for example, against the powdery mildew of apple causative organism (*Podosphaera leucotricha*), species of Botrytis, such as, for example, against the grey mould causative organism (*Botrytis cinerea*), and also for combating rice diseases, such as *Pyricularia oryzae* and *Pellicularia sasakii*. The compounds according to the invention also have a good action against Puccinia and *Pyrenophora teres* on cereal.

It should be emphasized that the substances according to the invention not only have a protective action, but in some cases also have a systemic action. It is thus possible to protect plants from fungal attack if the active compound is fed to the above-ground parts of the plants via the soil and the root or via the seed.

The active compounds can be converted to the customary formulations, such as solutions, emulsions, wettable powders, suspensions, powders, dusting agents, foams, pastes, soluble powders, granules, aerosols, suspension-emulsion concentrates, seed treatement powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02% by weight are required at the place of action.

PREPARATION EXAMPLES

EXAMPLE 1

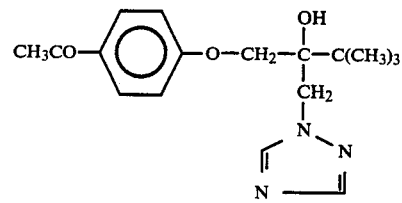

(Process b)

A solution of 28.96 g (0.16 mol) of 2-tert.-butyl-2-(1,2,4-triazol-1-yl-methyl)-oxirane in 50 ml of n-propanol is added dropwise to a solution of 24.5 g (0.18 mol) of p-hydroxyacetophenone and 0.46 g (0.02 mol) of sodium in 150 ml of n-propanol at room temperature, with stirring. The reaction mixture is then heated under reflux for 4 days. It is then concentrated, the residue is taken up in ethyl acetate and the mixture is washed twice with 1N sodium hydroxide solution, twice with water and once with saturated sodium chloride solution. The ethyl acetate phase is dried over sodium sulphate and concentrated. The residue is chromatographed over a silica gel column (methylene chloride-/ethyl acetate =4:1). The resulting product crystallizes after addition of ether. 26.9 g (53% of theory) of 2-(4- acetophenoxymethyl)-3,3-dimethyl-1-(1,2,4-triazol-1-yl)-2-butanol of melting point of 98°-99° C. are obtained.

EXAMPLE 2

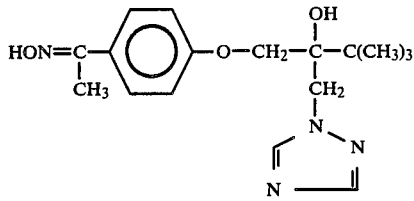

(Process c)

43.5 g (0.137 mol) of 2-(4-acetophenoxymethyl)-3,3-dimethyl-1-(1,2,4-triazol-1-yl)-2-butanol (Example 1), 14.28 g (0.2055 mol) of hydroxylamine hydrochloride and 16.85 g (0.2055 mol) of sodium acetate are dissolved in a mixture of 150 ml of water and 250 ml of ethanol and the solution is heated under reflux overnight. The reaction mixture is then concentrated, the residue is taken up in water/ethyl acetate and the mixture is rendered basic with 1N sodium hydroxide solution. The organic phase is separated off and the aqueous phase is extracted twice with ethyl acetate. The combined organic phases are washed once with dilute and twice with saturated sodium chloride solution, dried over sodium sulphate and concentrated. Recrystallization of the residue from acetonitrile gives 34.8 g (76.5% of theory) of 3,3-dimethyl-2-[4-(1-hydroximinoethyl)-phenoxymethyl]-1-(1,2,4-triazol-1-yl)-2-butanol of melting point 129°-132° C.

EXAMPLE 3

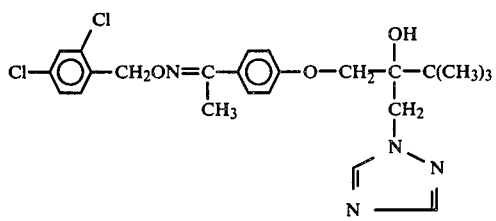

(Process d)

1.44 g (0.06 mol) of sodium hydride (30% strength in paraffin oil) are added to a solution of 14.94 g (0.045 mol) of 3,3-dimethyl-2-[4-(1-hydroximinoethyl)-phenoxymethyl]-1-(1,2,4-triazol-1-yl)-2-butanol (Example 2) in 120 ml of absolute dimethylsulphoxide. The reaction mixture is stirred at room temperature for about 1 hour, until a clear solution has formed. 3.33 ml (0.06 mol) of 2,4-dichlorobenzyl chloride are then added and the reaction mixture is subsequently stirred at room temperature for 1.5 hours. Thereafter, water and glacial acetic acid are carefully added and the mixture is concentrated. The residue is taken up in ethyl acetate and the mixture is washed several times with dilute sodium chloride solution, dried over sodium sulphate and concentrated. The residue is chromatographed over a silica gel column (methylene chloride/ethyl acetate=4:1) and the product is recrystallized from acetonitrile. 16.2 g (73% of theory) of 2-{4-[1-(2,4-dichlorobenzylimino)-ethyl]-phenoxymethyl}-3,3-dimethyl-1-(1,2,4-triazol-1-yl)-2-butanol of melting point 101° C. are obtained.

EXAMPLE 4

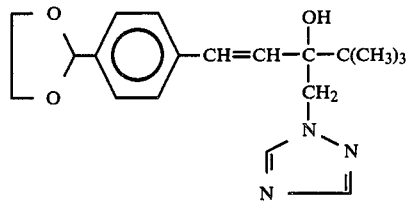

(Process a)

25.6 g (0.093 mol) of 2-{2-[4-(1,3-dioxolan-2-yl)-phenyl]-ethenyl}-2-tert.-butyl-oxirane in 47 ml of absolute dimethylformamide are added dropwise, at room temperature, to a solution of sodium triazolide, prepared by slowly introducing 12.9 g (0.187 mol) of 1,2,4-triazole into a suspension of 5.6 g (0.187 mol) of sodium hydride (80% strength in paraffin oil) in 187 ml of absolute dimethylformamide. The reaction mixture is stirred at 80° C. for 4 hours and left to stand overnight at room temperature. Thereafter, the reaction mixture is poured onto ice water and extracted several times with ethyl acetate. The combined ethyl acetate phases are washed twice with water and once with saturated sodium chloride solution, dried over sodium sulphate and concentrated. The residue is chromatographed over a silica gel column (methylene chloride/ethyl acetate=2:1) and the product is recrystallized from n-hexane/ethyl acetate. 7.75 g (24% of theory) of 3,3-dimethyl-2-{2-[4-(1,3-dioxolan-2-yl)-phenyl]-ethenyl}-1-(1,2,4-triazol-1-yl)-2-butanol of melting point 109.5°-110° C. are obtained.

Preparation of the starting substance

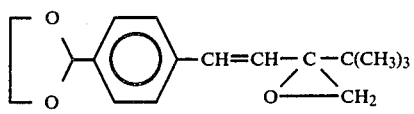

8.1 g (0.13 mol) of iodomethane are slowly added dropwise to a solution of 9.9 ml (0.135 mol) of dimethyl sulphide in 75 ml of absolute dimethylsulphoxide and 35 ml of absolute tetrahydrofuran, during which the internal temperature must not rise above 35° C. This suspension is subsequently stirred at room temperature overnight, and 15.7 g (0.14 mol) of potassium tert.-butylate are then added in portions. The mixture is subsequently stirred at room temperature for 30 minutes and cooled to 0° C., and 26 g (0.1 mol) of 4,4-dimethyl-1-[4-(1,3-dioxolan-2-yl)-phenyl]-1-penten-3-one are added in portions. The reaction mixture is subsequently stirred at room temperature overnight, water is then added and the mixture is extracted three times with toluene. The combined toluene phases are washed with water and saturated sodium chloride solution, dried over sodium sulphate and concentrated. 25.6 g of crude 2-{2-[4-(1,3-dioxolan-2-yl)-phenyl]-ethenyl}-2-tert.-butyl-oxirane are obtained as an oil, which is further reacted directly.

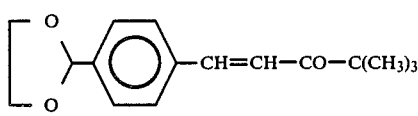

100 g (0.5612 mol) of 4-(1,3-dioxolan-2-yl)-benzaldehyde and 56.1 g (0.56 mol) of pinacoline are dissolved in a mixture of 280 ml of ethanol and 56 ml of water, and 17 ml of 10% strength sodium hydroxide solution are added at room temperature. The mixture is subsequently stirred for 1 hour, 0.56 g of solid sodium hydroxide are added and the mixture is subsequently stirred for 2 days. Thereafter, the precipitate is filtered off with suction, washed with 200 ml of ethanol/water (1:1) and then with water, dried and recrystallized twice from ethanol. 56.5 g (39% of theory) of 4,4-dimethyl-1-[4-(1,3-dioxolan-2-yl)-phenyl]-1-penten-3-one of melting point 79°–81° C. are obtained.

EXAMPLE 5

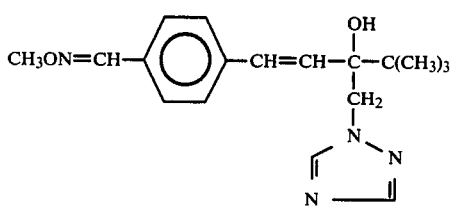

(Process c)

1 g (0.0029 mol) of 3,3-dimethyl-2-{2-[4-(1,3-dioxolan-2-yl)-phenyl]-ethenyl}-1-(1,2,4-triazol-1-yl)-2-butanol (Example 4), 0.42 g (0.005 mol) of O-methylhydroxylamine hydrochloride and 0.41 g (0.005 mol) of sodium acetate are dissolved in 20 ml of ethanol and 15 ml of water and the solution is heated under reflux for 2 hours. The reaction mixture is concentrated, the residue is taken up in ethyl acetate and the mixture is washed twice with water and once with saturated sodium chloride solution, dried over sodium sulphate and concentrated. The crystalline residue is washed with a little ether and recrystallized from n-hexane/ethyl acetate. 0.67 g (70% of theory) of 3,3-dimethyl-2-[2-(4-methoximinomethylphenyl)-ethenyl]-1-(1,2,4-triazol-1-yl)-2-butanol of melting point 140°–142° C. are obtained.

The following compounds of the general formula

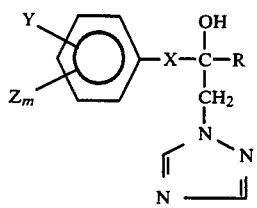

are obtained in an analogous manner corresponding to processes (a) to (d) according to the invention:

| Example No. | | Y | X | R | Melting point (°C.) or $n_D^{20}$ |
|---|---|---|---|---|---|
| 6 | 4-CH$_3$ON=CH— | — | —OCH$_2$— | —C(CH$_3$)$_3$ | 92–93 |
| 7 | 4-CH$_3$ON=C(CH$_3$)— | — | —OCH$_2$— | —C(CH$_3$)$_3$ | 92–94 |
| 8 | 4-CH$_2$=CH—CH$_2$ON=C(CH$_3$)— | — | —OCH$_2$— | —C(CH$_3$)$_3$ | 1.5445 |
| 9 | 4-CH$_3$CO— | — | —OCH$_2$— | —C(CH$_3$)$_2$CH$_2$F | 111 |
| 10 | 4-OHC— | — | —OCH$_2$— | —C(CH$_3$)$_3$ | 1.5491 |
| 11 | 4-CH$_3$CO— | — | —OCH$_2$— | —C(CH$_3$)$_2$CH$_2$OCH$_3$ | 80–81 |
| 12 | 4-OHC— | — | —OCH$_2$— | —C(CH$_3$)$_2$CH$_2$OCH$_3$ | 1.5457 |
| 13 | 4-CH$_3$ON=C(CH$_3$)— | — | —OCH$_2$— | —C(CH$_3$)$_2$CH$_2$F | 94.5–95 |
| 14 | 4-CH$_3$ON=CH | — | —CH$_2$CH$_2$— | —C(CH$_3$)$_3$ | 77–79 |
| 15 | 4-CH$_3$ON=CH— | — | —OCH$_2$— | —C(CH$_3$)$_2$CH$_2$OCH$_3$ | 1.5430 |
| 16 | 4-CH$_3$ON=C(CH$_3$)— | — | —OCH$_2$— | —C(CH$_3$)$_2$CH$_2$OCH$_3$ | 62–65 |
| 17 | 4-CH$_2$=CH—CH$_2$—ON=CH— | — | —OCH$_2$— | —C(CH$_3$)$_3$ | 1,5560 |
| 18 | 4-[C$_6$H$_4$-C(=NOCH$_3$)-] | — | —OCH$_2$— | —C(CH$_3$)$_3$ | 1,5692 |
| 19 | 3-[1,3-dioxolan-2-yl] | — | —OCH$_2$— | —C(CH$_3$)$_3$ | 73–75 |

-continued

| Example No. | | | | Melting point (°C.) or $n_D^{20}$ |
|---|---|---|---|---|
| 20 | 4-[O-C(=O)-O] | — | — | phenyl-Cl | 135–36.5 |
| 21 | 3-CH₃ON=CH— | — | —OCH₂— | —C(CH₃)₃ | 76–78 |
| 22 | 2-CH₃CO— | — | —OCH₂— | —C(CH₃)₃ | 105.5-07 |
| 23 | 2-CH₃ON=C(CH₃)— | — | —OCH₂— | —C(CH₃)₃ | 71–73 |

Use examples

The substances shown below are used as comparison compounds in the use examples which follow:

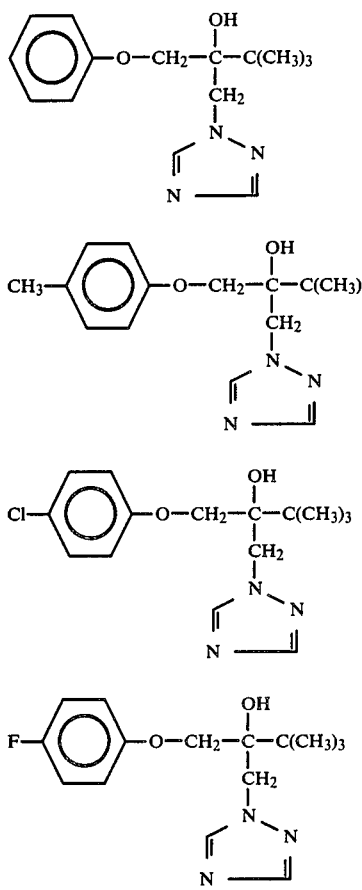

(A)

(B)

(C)

(D)

EXAMPLE A

*Cochliobolus sativus* test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humdity of about 80%.

Evaluation is carried out 7 days after the inoculation.

In this test, a clearly superior activity compared with the prior art is shown, for example, by the compounds according to the following preparation examples: 6 and 7.

EXAMPLE B

Erysiphe test (barley)/seed treatment

The active compounds are used as dry dressings. These are prepared by extending the particular active compound with a ground mineral to give a finely pulverulent mixture, which ensures uniform distribution on the seed surface.

To apply the dressing, the seed is shaken with the dressing in a closed glass flask for 3 minutes.

3 batches of 12 grains of the barley are sown 2 cm deep in standard soil. 7 days after sowing, when the young plants have unfolded their first leaf, they are dusted with spores of *Erysiphe graminis f.* sp. *hordei.*

The plants are placed in a greenhouse at a temperature of about 20° C. and a relative atmospheric humidity of about 30% in order to promote the development of powdery mildew pustules.

Evaluation is carried out 7 days after the inoculation.

In this test, a clearly superior activity compared with the prior art is shown, for example, by the compound according to the following preparation example: 7.

EXAMPLE C

*Drechslera graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compounds according to the following preparation examples: 6 and 7.

EXAMPLE D

Podosphaera test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the powdery mildew of apple causative organism (*Podosphaera leucotricha*).

The plants are then placed in a greenhouse at 23° C. and a relative atmospheric humdity of about 70%.

Evaluation is carried out 9 days after the inoculation.

In this test, a clearly superior activity compared with the prior art is shown, for example, by the compounds according to the following preparation examples: 7 and 6.

EXAMPLE E

Botrytis test (bean)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humidity chamber at 20° C. 3 days after the inoculation, the size of the infected spots on the leaves is evaluated.

In this test a clearly superior activity compared with the prior art is shown, for example, by the compound according to the following preparation example: 6.

EXAMPLE F

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a good activity is shown, for example by the compound according to the following preparation example: 6.

EXAMPLE G

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compound according to the following preparation example: 7.

EXAMPLE H

Pellicularia test (rice)
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with *Pellicularia sasakii* and are placed at 25° C. and 100% relative atmospheric humidity.

The evaluation of the disease infestation is carried out 5 to 8 days after the inoculation.

In this test, a good activity is shown, for example, by the compound according to the following preparation example: 6.

It will be appreciated that the instant specification and examples are set forth by way of illustration and not limitation, and that various modifications and changes may be made without departing from the spirit and scope of the present invention.

We claim:

1. A substituted 1-hydroxyethyl-triazolyl derivative of the formula $$\begin{array}{c} Y \\ Z_m \end{array} \diagup\!\!\!\!\bigcirc\!\!\!\!\diagdown X-\underset{\underset{CH_2}{|}}{\overset{\overset{OH}{|}}{C}}-R \\ \qquad\qquad\qquad \underset{N\underline{\quad\quad}}{\underset{\|}{N}}\diagdown_N$$

in which
- R represents isopropyl, or represents cyclopropyl, cyclopentyl or cyclohexyl, in each case optionally mono-, di- or tri-substituted by identical or different substituents from the group consisting of methyl, ethyl, isopropyl, methoxy and ethoxy, or represents phenyl which is optionally mono-, di- or tri-substituted by identical or different substituents from the group consisting of fluorine, chlorine, methyl, trifluoromethyl, phenyl and chlorophenyl, or represents the grouping $$-\underset{\underset{CH_2R^2}{|}}{\overset{\overset{CH_2R^1}{|}}{C}}-CH_3 \quad \text{or} \quad -\underset{\underset{CH_3}{|}}{\overset{\overset{CH_3}{|}}{C}}(CH_2)_n-R^3;$$

wherein
- $R^1$ represents hydrogen, fluorine or chlorine;
- $R^2$ represents fluorine or chlorine;
- $R^3$ represents methyl, ethyl, propyl, methoxy, ethoxy, methylthio, ethylthio, trifluoromethoxy, trifluoromethylthio, vinyl, methoxycarbonyl, ethoxycarbonyl or cyano, or represents phenyl, phenoxy, phenylthio, phenylmethoxy or phenylmethylthio, it being possible for the last five radicals mentioned to be substituted by fluorine, chlorine, methyl, ethyl, methoxy, methylthio, trifluoromethyl, trifluoromethoxy, trifluoromethylthio, dimethylamino, methoxycarbonyl and ethoxycarbonyl; and
- n represents the number 0, 1 or 2;
- X represents the grouping —OCH₂—, —SCH₂—, —(CH₂)ₚ or —CH=CH—;
- Y represents the grouping —CO—Y¹, —C(OR⁴)₂—Y¹ or $$-\underset{\underset{\diagdown O \diagup}{|}}{\overset{\overset{Y^1}{|}}{C}}\overset{O\diagdown}{\diagup}(CH_2)_q,$$

or the grouping —C(Y¹)=N—OY²;
- Y¹ represents hydrogen, methyl, ethyl or isopropyl, or represents phenyl, which is optionally mono- or di-substituted by identical or different substituents from the group consisting of fluorine, chlorine methyl and trifluoromethyl;
- Y² represents hydrogen, methyl, ethyl, n-propyl, n-butyl, allyl or propargyl, or represents benzyl which is optionally mono- or di-substituted by identical or different substituents from the group consisting of fluorine, chlorine, methyl, trifluoromethyl and trifluoromethoxy;
- R⁴ represents methyl, ethyl or propyl;
- q represents the number 2 or 3;
- Z represents fluorine, chlorine, bromine, methyl, methoxy, methylthio, trifluoromethyl, trifluoromethoxy or trifluoromethylthio,
- m represents the number 0, 1 or 2; and
- p represents the number 0, 1 or 2, or an addition product thereof with an acid or metal salt.

2. A compound according to claim 1, wherein such compound is
3,3-dimethyl-2-(2-(4-methoximinomethylphenyl)-ethenyl)-1-(1,2,4-triazol-1-yl)-2-butanol of the formula $$CH_3ON=CH-\!\!\bigcirc\!\!-CH=CH-\underset{\underset{CH_2}{|}}{\overset{\overset{OH}{|}}{C}}-C(CH_3)_3 \\ \qquad\qquad\qquad\qquad \underset{N\underline{\quad\quad}}{\underset{\|}{N}}\diagdown_N$$

or an addition product thereof with an acid or metal salt.

3. A compound according to claim 1, wherein such compound is
3,3-dimethyl-2-(4-methoximinomethylphenoxymethyl)-1-(1,2,4-triazol-1-yl)-2-butanol of the formula $$CH_3ON=CH-\!\!\bigcirc\!\!-O-CH_2-\underset{\underset{CH_2}{|}}{\overset{\overset{OH}{|}}{C}}-C(CH_3)_3 \\ \qquad\qquad\qquad\qquad \underset{N\underline{\quad\quad}}{\underset{\|}{N}}\diagdown_N$$

or an addition product thereof with an acid or metal salt.

4. A compound according to claim 1, wherein such compound is
3,3-dimethyl-2-(4-(1-methoximinoethyl)-phenoxymethyl)-1-(1,2,4-triazol-1-yl)-2-butanol of the formula $$CH_3ON=\underset{\underset{CH_3}{|}}{\overset{\overset{CH_3}{|}}{C}}-\!\!\bigcirc\!\!-O-CH_2-\underset{\underset{CH_2}{|}}{\overset{\overset{OH}{|}}{C}}-C(CH_3)_3 \\ \qquad\qquad\qquad\qquad\qquad \underset{N\underline{\quad\quad}}{\underset{\|}{N}}\diagdown_N$$

or an addition product thereof with an acid or metal salt.

5. A compound according to claim 1, wherein such compound is
3,3-dimethyl-2-(4-(1-allyloximinoethyl)-phenoxymethyl)-1-(1,2,4-triazol-1-yl)-2-butanol of the formula

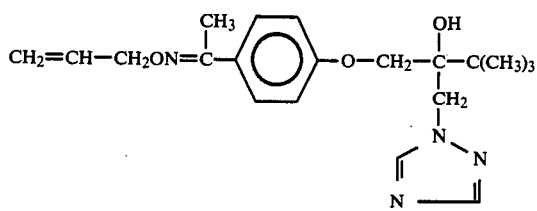

or and addition product thereof with an acid or metal salt.

6. A fungicidal composition comprising a fungicidally effective amount of a compound or addition product according to claim 1 in admixture with a diluent.

7. A method of combating fungi which comprises administering to such fungi or to a fungus habitat a fungicidally effective amount of a compound or addition product according to claim 2.

8. The method according to claim 7, wherein such compound is 3,3-dimethyl-2-(2-(4-methoximinomethylphenyl)ethenyl)-1-(1,2,4-triazol-1-yl)-2-butanol, 3,3-dimethyl-2-(4-methoximinomethylphenoxymethyl)-1-(1,2,4-triazol-1-yl)-2-butanol, 3,3-dimethyl-2-(4-(1-methoximinoethyl)-phenoxymethyl)-1-(1,2,4-triazol-1-yl)-2-butanol or 3,3-dimethyl-2-(4-(1-allyloximinoethyl)-phenoxymethyl)-1-(1,2,4-triazol-1-yl)-2-butanol, or an addition product thereof with an acid or metal salt.

* * * * *